(12) United States Patent
Essayed et al.

(10) Patent No.: US 10,881,513 B2
(45) Date of Patent: Jan. 5, 2021

(54) PROSTHESES USING INDIVIDUAL-SPECIFIC 3D PRINTED MODEL

(71) Applicant: The Brigham and Women's Hospital, Inc., Boston, MA (US)

(72) Inventors: Walid Ibn. Essayed, Cambridge, MA (US); Prashin Unadkat, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 92 days.

(21) Appl. No.: 16/122,823

(22) Filed: Sep. 5, 2018

(65) Prior Publication Data
US 2019/0076254 A1 Mar. 14, 2019

Related U.S. Application Data

(60) Provisional application No. 62/554,392, filed on Sep. 5, 2017.

(51) Int. Cl.
*A61F 2/28* (2006.01)
*B33Y 50/02* (2015.01)
(Continued)

(52) U.S. Cl.
CPC ............ *A61F 2/2875* (2013.01); *B33Y 10/00* (2014.12); *B33Y 50/00* (2014.12); *B33Y 50/02* (2014.12); *B33Y 80/00* (2014.12); *A61F 2/30942* (2013.01); *A61F 2002/2885* (2013.01); *A61F 2002/30962* (2013.01); *B29C 64/386* (2017.08)

(58) Field of Classification Search
CPC .................. A61F 2/2875; A61F 2/2846; A61F 2250/0029; A61F 2250/0018; A61F 2002/285; A61F 2/07
See application file for complete search history.

(56) References Cited

U.S. PATENT DOCUMENTS 10,179,050 B2 * 1/2019 Scrantz ................ A61F 2/2875
10,426,917 B2 * 10/2019 Porter ................... A61M 25/00
(Continued)

OTHER PUBLICATIONS

Ahmed, Oh, et al. "Efficacy of perioperative lumbar drainage following endonasal endoscopic cerebrospinal fluid leak repair: a meta-analysis." Otolaryngology—Head and Neck Surgery 156.1 (2017): 52-60.

(Continued)

*Primary Examiner* — Brian A Dukert
*Assistant Examiner* — Amanda M Barkan
(74) *Attorney, Agent, or Firm* — Quarles & Brady LLP

(57) ABSTRACT

A prosthetic device includes a first material and a second material that surrounds a least a portion of the perimeter of the first material. The first material and the second material have a resting shape that is configured to fit a body part on which the prosthetic devices is to be implanted. The second material is deformable to fit the prosthetic device through an opening of the subject smaller than the resting shape to reach the body part. A prosthetic device can be produced by obtaining image data corresponding to a body part of the subject, generating and refining one or more models of a body part based on the image data, and producing the prosthetic device as a three-dimensional print of the refined model.

13 Claims, 11 Drawing Sheets

(51) Int. Cl.
  B33Y 50/00   (2015.01)
  B33Y 10/00   (2015.01)
  B33Y 80/00   (2015.01)
  B29C 64/386  (2017.01)
  A61F 2/30    (2006.01)

(56) References Cited

U.S. PATENT DOCUMENTS

| | | | | |
|---|---|---|---|---|
| 10,575,975 | B2* | 3/2020 | Thapliyal | A61F 2/966 |
| 2007/0270841 | A1* | 11/2007 | Badie | A61B 17/8061 |
| | | | | 606/86 A |
| 2019/0231531 | A1* | 8/2019 | Gordon | A61F 2/0059 |

OTHER PUBLICATIONS

Alvarez Berastegui Gr, et al: Endonasal endoscopic transsphenoidal chiasmapexy using a clival cranial base cranioplasty for visual loss from massive empty sella following macroprolactinoma treatment with bromocriptine: case report. J Neurosurg 124:1025-1031, 2016.

Banu Ma, et al: Low-dose intrathecal fluorescein and etiology-based graft choice in endoscopic endonasal closure of CSF leaks. Clin Neurol Neurosurg 116:28-34, 2014.

Bartlett Nw, et al: Soft Robotics. A 3D-printed, functionally graded soft robot powered by combustion. Science 349:161-165, 2015.

Bedrosian Jc, et al: The endoscopic endonasal approach to repair of iatrogenic and noniatrogenic cerebrospinal fluid leaks and encephaloceles of the anterior cranial fossa. World Neurosurg 82:S86-94, 2014.

Cappabianca P, et al: Endoscopic endonasal transsphenoidal approach: an additional reason in support of surgery in the management of pituitary lesions. Skull Base Surg 9:109-117, 1999.

Cappabianca P, et al: Sellar repair in endoscopic endonasal transsphenoidal surgery: results of 170 cases. Neurosurgery 51.6 (2002): 1365-1372.

Cavallo Lm, et al: Skull base reconstruction in the extended endoscopic transsphenoidal approach for suprasellar lesions. J Neurosurg 107:713-720, 2007.

Dhandapani S, et al: Endonasal Endoscopic Transsphenoidal Resection of Tuberculum Sella Meningioma with Anterior Cerebral Artery Encasement. Cureus 7:e311, 2015.

Eloy Ja, et al: Challenges and surgical nuances in reconstruction of large planum sphenoidale tuberculum sellae defects after endoscopic endonasal resection of parasellar skull base tumors. Laryngoscope 123:1353-1360, 2013.

Essayed Wi, et al: Endoscopic endonasal approach to the ventral brainstem: anatomical feasibility and surgical limitations. J Neurosurg:1-8, 2017.

Fahmy Md, et al: Three-Dimensional Bioprinting Materials with Potential Application in Preprosthetic Surgery. J Prosthodont 25:310-318, 2016.

Fedorov A, et al: 3D Slicer as an image computing platform for the Quantitative Imaging Network. Magn Reson maging 30:1323-1341, 2012.

Fraser Jf, et al: Endoscopic endonasal transclival resection of chordomas: operative technique, clinical outcome, and review of the literature. J Neurosurg 112:1061-1069, 2010.

Garcia-Navarro V, et al: Gasket seal closure for extended endonasal endoscopic skull base surgery: efficacy in a large case series. World Neurosurg 80:563-568, 2013.

Gladman As, et al: Biomimetic 4D printing. Nat Mater 15:413-418, 2016.

Guiducci L, et al: The Geometric Design and Fabrication of Actuating Cellular Structures. Advanced Materials Interfaces 2.11 (2015): 1500011.

Hadad G, et al: A novel reconstructive technique after endoscopic expanded endonasal approaches: vascular pedicle nasoseptal flap. Laryngoscope 116:1882-1886, 2006.

Harvey Rj, et al: Endoscopic skull base reconstruction of large dural defects: a systematic review of published evidence. Laryngoscope 122:452-459, 2012.

Hung Bp, et al: Three-Dimensional Printing of Bone Extracellular Matrix for Craniofacial Regeneration. ACS Biomater Sci Eng 2:1806-1816, 2016.

Jeswani S, et al: Comparative analysis of outcomes following craniotomy and expanded endoscopic endonasal transsphenoidal resection of craniopharyngioma and related tumors: a single-institution study. J Neurosurg 124:627-638, 2016.

Komotar Rj, et al: The endoscope-assisted ventral approach compared with open microscope-assisted surgery for clival chordomas. World Neurosurg 76:318-327; discussion 259-362, 2011.

Kong Ds, et al: Challenging reconstructive techniques for skull base defect following endoscopic endonasal approaches. Acta Neurochir (Wien) 153:807-813, 2011.

Koutourousiou M, et al: Endoscopic endonasal surgery for craniopharyngiomas: surgical outcome in 64 patients. J Neurosurg 119:1194-1207, 2013.

Lee Sj, et al: Surface modification of 3D-printed porous scaffolds via mussel-inspired polydopamine and effective immobilization of rhBMP-2 to promote osteogenic differentiation for bone tissue engineering. Acta 36 Biomater 40:182-191, 2016.

Leng Lz, et al: Endoscopic, endonasal resection of craniopharyngiomas: analysis of outcome including extent of resection, cerebrospinal fluid leak, return to preoperative productivity, and body mass index. Neurosurgery 70:110-123; discussion 123-114, 2012.

Linsler S, et al: Endoscopic Endonasal Transclival Resection of a Brainstem Cavemoma: A Detailed Account of Our Technique and Comparison with the Literature. World Neurosurg 84:2064-2071, 2015.

Luginbuhl Aj, et al: Endoscopic repair of high-flow cranial base defects using a bilayer button. Laryngoscope 120:876-880, 2010.

Mascarenhas L, et al: The transplanum transtuberculum approaches for suprasellar and sellar-suprasellar lesions: avoidance of cerebrospinal fluid leak and lessons learned. World Neurosurg 82:186-195, 2014.

Nyberg E, et al: Comparison of 3D-Printed Poly-epsilon- caprolactone Scaffolds Functionalized with Tricalcium Phosphate, Hydroxyapatite, Bio-Oss, or Decellularized Bone Matrix. Tissue Eng Part A, 2016.

Olson Dr, et al: The symptomatic empty sella. Prevention and correction via the transsphenoidal approach. J Neurosurg 37:533-537, 1972.

Rajappa P, et al: Endoscopic endonasal transclival approach to a ventral pontine pediatric ependymoma. J Neurosurg Pediatr 12:465-468, 2013.

Randazzo M, et al: 3D printing in neurosurgery: A systematic review. Surg Neurol Int 7:S801-s809, 2016.

Raza Sm, et al: Multi-layer reconstruction during endoscopic endonasal surgery: how much is necessary? World Neurosurg 83:138-139, 2015.

Raza Sm, et al: Sensitivity and specificity of intrathecal fluorescein and white light excitation for detecting intraoperative cerebrospinal fluid leak in endoscopic skull base surgery: a prospective study. J Neurosurg 124:621-626, 2016.

Roy Td, et al: Performance of degradable composite bone repair products made via three-dimensional fabrication techniques. J Biomed Mater Res A 66:283-291, 2003.

Sigler Ac, et al: Endoscopic Skull Base Reconstruction: An Evolution of Materials and Methods. Otolaryngol Clin North Am, 2017.

Tibbits S: 4D Printing: Multi-Material Shape Change. Architectural Design 84:116-121, 405 2014.

Vellutini Ede A, et al: The endoscopic endonasal approach for extradural and intradural clivus lesions. World Neurosurg 82:S106-115, 408 2014.

Wannemuehler Tj, et al: Outcomes in transcranial microsurgery versus extended endoscopic endonasal approach for primary resection of adult craniopharyngiomas. Neurosurg Focus 41:E6, 2016.

Zwagerman Nt, et al: Endoscopic transnasal skull base surgery: pushing the boundaries. J Neurooncol 130:319-330, 2016.

* cited by examiner

PROSTHESES USING INDIVIDUAL-SPECIFIC 3D PRINTED MODEL

CROSS-REFERENCE

This application claims priority under 35 U.S.C. § 119 to U.S. Provisional Patent Application No. 62/554,392 filed on Sep. 5, 2017, the entire contents of which is incorporated herein by reference.

STATEMENT REGARDING FEDERALLY FUNDED RESEARCH

This invention was made with government support under R25, NCIGT P41 awarded by the National Institutes of Health. The government has certain rights in the invention.

FIELD OF THE INVENTION

The present invention relates generally to the reconstruction of body defects, and in particular, reconstruction of skull-base defects using individual-specific prosthesis modeling.

BACKGROUND OF THE INVENTION

In recent years, endoscopic endonasal approaches have become a key option for the surgical treatment of multiple skull base pathologies such as pituitary adenomas, craniopharyngiomas, chordomas, meningiomas, sinonasal malignancy, and multiple other lesions. As they developed, these approaches extended beyond the sella to the anterior and posterior skull base compartments through progressively more complex corridors requiring larger areas of bone removal. The size and shape of these skull base defects vary according to, for example, tumor location, the tumor's relationships to various vasculo-nervous structures, and the specific nasal and bony anatomy of the patient.

The quality of the skull base reconstruction of a defect is crucial to avoid postoperative cerebrospinal fluid (CSF) leaks and associated meningitis, representing one of the major challenges to endoscopic skull base surgery. Recently, the development of multilayer reconstruction techniques, such as the "gasket seal" technique and the "button technique," have led to improvements in skull base reconstructions.

For a gasket seal closure, a surgeon wedges a plate in the skull base defect after overlaying a fascia lata graft over the defect, creating a gasket. However, as defects can extend across different compartments of the skull base in larger approaches, the probability of all defect edges aligning on the same plane decreases, leading to instability and weak points around the gasket edges.

The button technique uses two layers of fascia lata graft sewed together at their center to repair defects. One layer is lodged in the intradural space while the second layer is spread over the other side of the bony defect. However, the flexibility of the two fascia lata graft layers can lead to progressive dislodgement from normal CSF pulsations and perioperative pressure surges.

Therefore, it would be desirable to have a skull base defect reconstruction technique capable of conforming to specific three-dimensional (3D) variations of large defects with sufficient rigidity and minimal risk of post-operative CSF leaks.

SUMMARY OF THE INVENTION

The present invention provides a method for making and using a patient-specific prosthetic device for repairing defects in bony body parts. The prosthetic device can be designed to fit the anatomy of a particular subject, and can then be printed with a three-dimensional (3D) printer. Additionally, intraoperative neuronavigation techniques can be utilized to further tailor the prosthetic device in addition to guiding its placement.

The prosthetic device includes a rigid core for supporting the device and a flexible edge that can conform to a body part to form a watertight seal. The flexible edges further allow the prosthetic device to be inserted into a subject via small openings. A series of handles on the prosthetic device enable easy and precise maneuvering of the device and aid in alignment of the device using intraoperative CT scans.

In accordance with one aspect of the invention, a prosthetic device for a subject includes a first material and a second material surrounding a least a portion of a perimeter of the first material. The first material and the second material have a resting shape configured to fit a body part of the subject. The second material is more flexible than the first material and deformable to fit the prosthetic device through an opening of the subject smaller than the resting shape to reach the body part.

In some forms, the prosthetic device includes one or more handles coupled to one of the first material and the second material.

In some forms, the second material is progressively more flexible from an inner edge adjacent the first material to an outer edge.

In some forms, an interface between the first material and the second material is an abrupt change from the first material to the second material. In some forms, an interface between the first material and the second material is a gradual change from the first material to the second material.

In some forms, the resting shape is modeled using CT imaging of the subject. In some forms, the resting shape is formed using three-dimensional printing.

In some forms, the resting shape generally matches a portion of the subject's skull. In some forms, the resting shape includes one or more characteristics that differ from an anatomical feature of the subject's skull. In some forms, the anatomical feature is a sella.

According to another aspect of the invention, a method of producing a prosthetic device for a subject includes the steps of obtaining image data corresponding to a body part of the subject, generating a first model of the body part based on the image data, generating a second model of the body part based on the image data that differs from the first model, and producing the prosthetic device as a three-dimensional print of the second model.

In some forms, the method includes implanting the prosthetic device in the subject. In some forms, the method includes adjusting a shape of the prosthetic device prior to implanting the prosthetic device.

In some forms, the method includes acquiring the image data preoperatively before an implantation procedure. In some forms, the method includes acquiring the image data intraoperatively during an implantation procedure. In some forms, the body part is a skull of the subject.

In some forms, the method includes increasing a size of the second model compared to the first model.

In some forms, the method includes adding one or more handles to the prosthetic device.

In some forms, generating the second model includes smoothing out one or more anatomical features of the first model.

In some forms, one of generating the first model and generating the second model includes mapping a first portion to include a first material and a second portion surrounding the first portion to include a second material; and creating the three-dimensional printed model of the prosthetic device includes creating the three-dimensional printed model with the first material and the second material.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
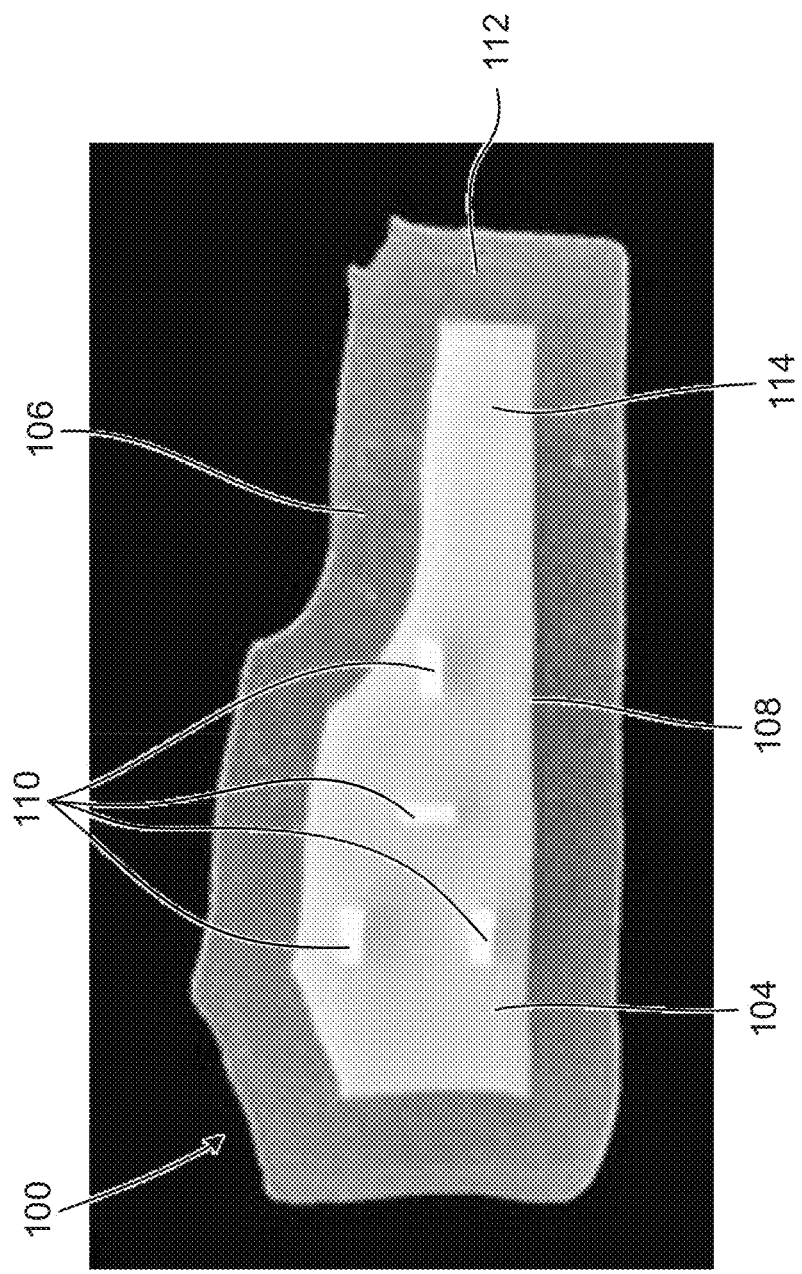
FIG. 1 is a top-down plan view of a prosthetic device.

The various aspects of the subject technology are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

Unless otherwise specified or limited, the terms "connected," and "coupled" and variations thereof are used broadly and encompass both direct and indirect mountings, connections, supports, and couplings. Further, "connected" and "coupled" are not restricted to physical or mechanical connections or couplings. As used herein, unless expressly stated otherwise, "connected" means that one element/feature is directly or indirectly connected to another element/feature, and not necessarily electrically or mechanically. Likewise, unless expressly stated otherwise, "coupled" means that one element/feature is directly or indirectly coupled to another element/feature, and not necessarily electrically or mechanically.

Referring now to the figures, and in particular FIG. 1, an exemplary embodiment of a prosthetic device 100 is illustrated. The prosthetic device 100 includes a first material 104 and a second material 106 arranged around a perimeter 108 of the first material 104. Further, the prosthetic device 100 can include one or more handles 100, such as four handles 110, arranged on the first material 104 and protruding outwardly therefrom. Each handle 110 is substantially perpendicular to the portion of the ventral surface of the prosthetic device 100 from which the handle 108 extends.

In other embodiments, the prosthetic device 100 can include the same or a different number of handles 110 as the illustrated embodiment, such as one, two, three, five, six, seven, or more handles. The handles 110 can be positioned on and coupled to the first material 104, the second material 106, or a combination thereof. Further, each of the handles 110 may extend outwardly from a surface of the prosthetic device 100 perpendicularly or at an angle other than ninety degrees. As further described below, the handles 119 can allow a surgeon to better maneuver and place the prosthetic device 100 in tight spaces. Additionally, in some embodiments, the second material 106 may only surround a portion of the perimeter 108 of the first material 104.

With continued reference to FIG. 1, the first material 104 and the second material 106 are made from different materials (that is, the materials 104, 106 include different properties). For example, the first material 104 may be rigid or semi-rigid, while the second material 106 may be more flexible than the first material 104, thereby enabling the prosthetic device 100 (or at least a portion thereof) to flex without breaking. More specifically, in some aspects, the second material 106 is configured to be more flexible than the first material 104, thereby providing a flexible edge 112 around a semi-rigid interior 114 defined by the first material 104. In some embodiments, the first material 104 and/or the second material 106 can naturally return to a resting shape (e.g., the shape illustrated in FIG. 1) after being deformed. As described below, this resting shape can be configured to fit to a body part of a subject. In other embodiments, however, the first material 104 and the second material 106 may need to be manually returned to a resting shape (for example, by a surgeon during implantation of the prosthetic device 100).

Figure 2A:
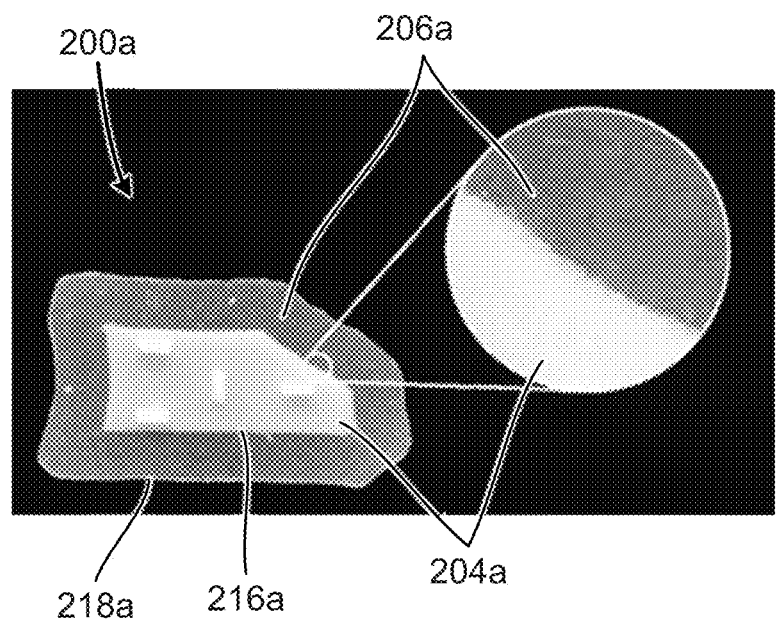
FIGS. 2A and 2B are top-down plan views of other prosthetic devices.
Figure 2B:
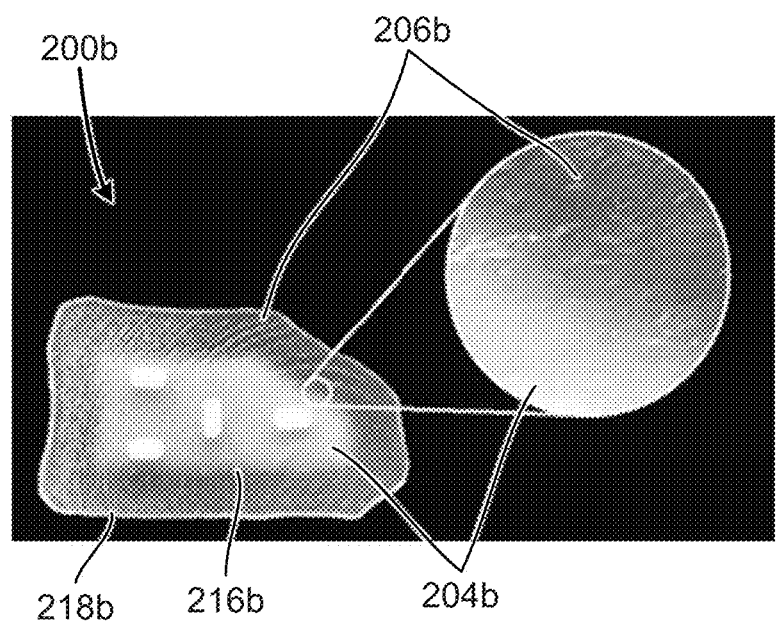

Referring now to FIGS. 2A and 2B, details of an interface between a first material and a second material of a prosthetic device are illustrated. FIG. 2A illustrates an embodiment of a prosthetic device 200a having an abrupt first material-second material transition (similar to the prosthetic device 100 of FIG. 1), and FIG. 2b illustrates a prosthetic device 200b having a gradual first material-second material transition. Looking first to FIG. 2A, the abrupt transition from the first material 204a to the second material 206a provides an abrupt increase in the flexibility of the prosthetic device 200a at a perimeter 208a of the first material 204a. This rapid increase in flexibility enables significant deformation of the second material 206a, thereby enabling significant changes of the lateral and longitudinal dimensions of the prosthetic device 200a. Additionally, in some embodiments, the flexibility of second material 206a is substantially consistent and does not significantly change between an inner edge 216a adjacent the first material 204a and an outer edge 218a distal from the first material 204a.

Looking to FIG. 2B, the gradual transition from the first material 204b to the second material 206b provides a gradual change in flexibility of the prosthetic device 200b. Furthermore, the second material 206b becomes progressively more flexible from the inner edge 216b to the outer edge 218b thereof. This gradual increase in flexibility evenly can distribute tension across the second material 206b, thereby reducing, and in some cases eliminating, stress concentrations within the second material 206b and along the perimeter 208b of the first material 204b (e.g., compared to an abrupt transition at the perimeter 208a of the first material 204a shown in FIG. 2A). The gradual increase in flexibility also enables significant deformation of the second material 206b, enabling significant changes of the lateral and longitudinal dimensions of the prosthetic device 200a.

In the embodiments illustrated in FIGS. 1-2B, flexibility differences between the first and second materials generally result from the use of different materials to make the first and second materials. In other embodiments, however, the flexibility differences can be achieved through alternative means. For example the first material and the second material can be composed of the same substance, but have different dimensions (e.g. different thicknesses), different structures, or be formed with different processes which result in flexibility differences. Further, some embodiments can be configured with an abrupt first material-second material transition and a gradual flexibility change of the second material from its inner edge to its outer edge, or with a gradual first material-second material transition and a constant flexibility of the second material after the transition. Further still, some embodiments may have some portions with gradual flexibility and/or first material-second material transitions as well as other portions with abrupt flexibility and/or first material-second material transitions.

Figure 3:
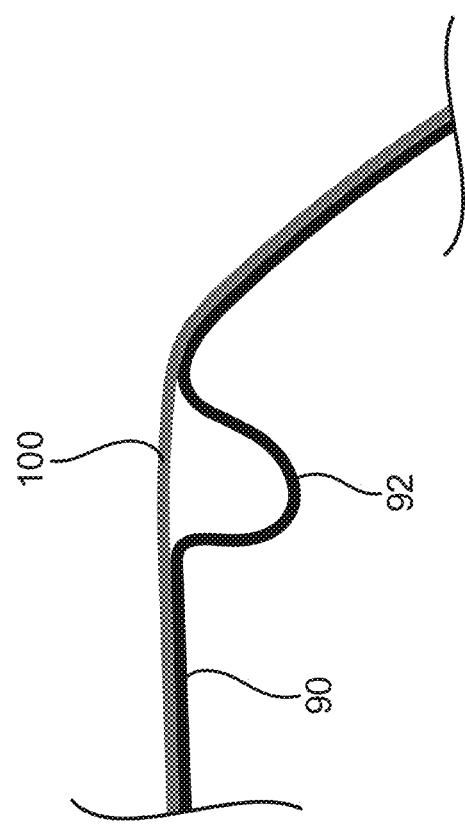
FIG. 3 is a schematic cross-sectional view of the prosthetic device of FIG. 1 fit to the base of a skull.

Generally, the resting shape of the prosthetic device 100 can be modeled using imaging data of the subject, thereby creating an individual-specific model, and produced using three-dimensional printing. By way of example, referring to FIGS. 1 and 3, (but similarly applicable to the embodiments of FIGS. 2A and 2B), the prosthetic device 100 can be configured for endoscopic endonasal reconstruction of a defect (not shown) of a skull base 90 in a subject. The first material 104 and the second material 106 can be formed so that the resting shape generally conforms to a base of the subject's skull 90 so that the prosthetic device can be placed thereon. The resting shape of the prosthetic device 100 can also be configured to include one or more characteristics that differ from anatomical features of the subject's skull 90. For example, as shown in FIG. 3, the resting shape of the prosthetic device 100 can be configured to circumvent the outpouching of the sella 92. In other words, this feature is "smoothed out" in the prosthetic device 100. Doing so can significantly reduce the accumulation of cerebrospinal fluid (or any other fluid) against the prosthetic device, thereby reducing the risk of an infection.

Due to its flexibility, the second material 106 can be sufficiently deformed so that the prosthetic device 100 can be introduced through an opening of a subject smaller than the resting shape in order to reach a desired location within the subject. For example, purely rigid models of extended defects can be impossible to introduce through a nostril and would be difficult to maneuver through the nasal cavity, with increased risk of mucosal injury. Here, however, the second material 106 of some embodiments can be sufficiently deformed so that the prosthetic device 100 can be introduced through a nostril and maneuvered through the nasal cavity of the subject, both of which are smaller than the resting shape of the first and second materials 104, 106. The handles 110 protruding from the ventral surface of the prosthetic device 100 enable the precise movement and placement of the prosthetic device 100 within the subject (e.g., by a surgeon) in the limited space available via this endonasal approach. Once in position near the skull base defect, the first and second materials 104, 106 can return (or be manually returned) to the resting shape and the prosthetic device 100 can be maneuvered into position on the defect. The flexible edges 112 of the prosthetic device 100 conform to the subject's anatomy, forming a watertight seal with the skull base 90, while the rigid interior 114 provides the required rigidity to hold the prosthetic device 100 in place without sagging. Additionally, in some embodiments, the first material 104 and/or the second material 106 can be transparent or semi-transparent to further aid navigation during implantation.

In some embodiments, a prosthetic device can be configured for use in the repair of different surgical and non-surgical defects. Some embodiments can include a first material and a second material that have a resting shape configured to fit different regions of the skull or a different bony body part, including any cavities formed within or by the body parts. Further, in some embodiments, a prosthetic device may incorporate biocompatible scaffold materials to support tissue ingrowth and/or swellable polymers for a more secure and adaptable fit.

As noted above, in some embodiments, a prosthetic device can have a resting shape configured to conform to substantially all of the anatomical features of the body part on which it is to be placed. For example, the resting shape can generally match a portion of a subject's skull. However, in other embodiments, the resting shape can be configured to have one or more characteristics that differ from an anatomical feature of the body part. For example, a resting shape could conform to a cavity or it could pass across the opening of the cavity. A prosthetic device could also differ from an anatomical feature of the body part to prevent the accumulation of any fluids.

Figure 4:
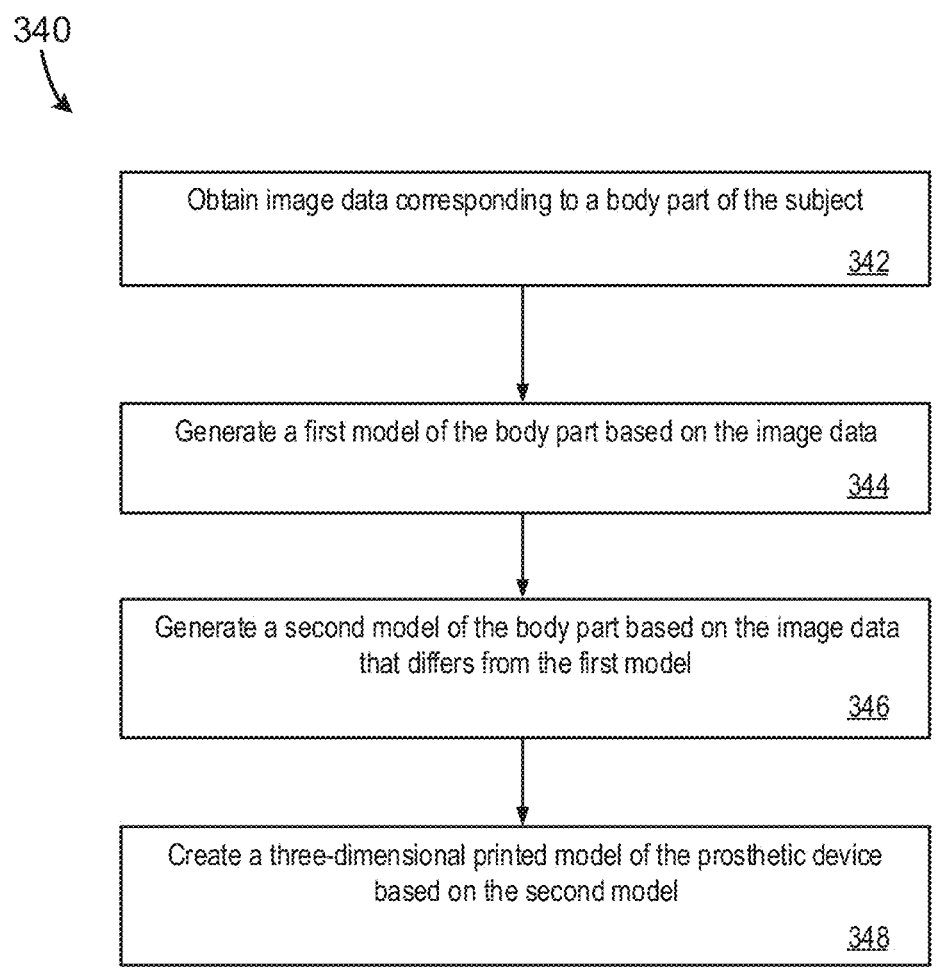
FIG. 4 is a process diagram of a method for producing a prosthetic device.

Referring now to FIG. 4, a general method 340 for producing a prosthetic device for a subject is illustrated. In step 342, image data corresponding to a body part of the subject is obtained. In the illustrated embodiment, one or more computed tomography (CT) scans are used to obtain this image data, however, in other embodiments, alternative imaging techniques, such as radiography or alternative tomographic approaches may be used.

Figure 5:
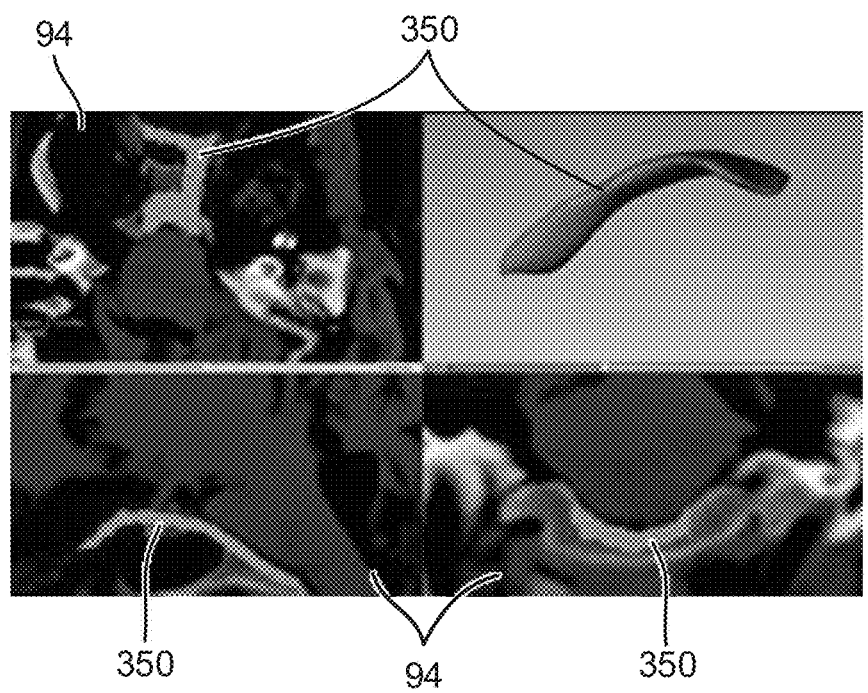
FIG. 5 is an example image illustrating a model produced according to the method of FIG. 4.
Figure 6:
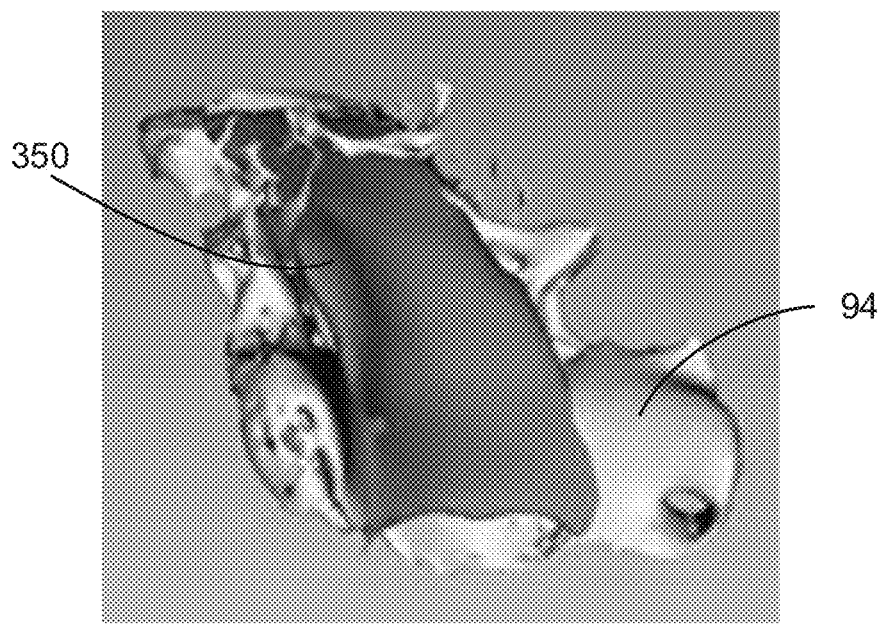
FIG. 6 is another example image illustrating a model produced according to the method of FIG. 4.

Based on the acquired image data, a first model of the subject's body part is generated in step 344. In step 346, a second model of the body part is generated that is based on the first model and the image data, but differs from the first model. For example, in some embodiments, generating the second model can include enlarging, shrinking, and/or smoothing out one or more anatomical features of the first model. The second model can also include additional features, such as handles placed at specific landmarks. Once generated, the second model is then used to create a 3D-printed model of the prosthetic device at step 348. Once printed, the prosthetic device can be implanted to fit the body part of the subject. Additionally, in some embodiments, the prosthetic device can be further tailored after printing and before implantation (e.g., adjusting its shape, for example, via manual manipulation, such as manually cutting edges of the device). A body part 94 of a subject and a model of a prosthetic device 350 generated using the method 340 of FIG. 4 are illustrated in FIGS. 5 and 6.

Figure 7:
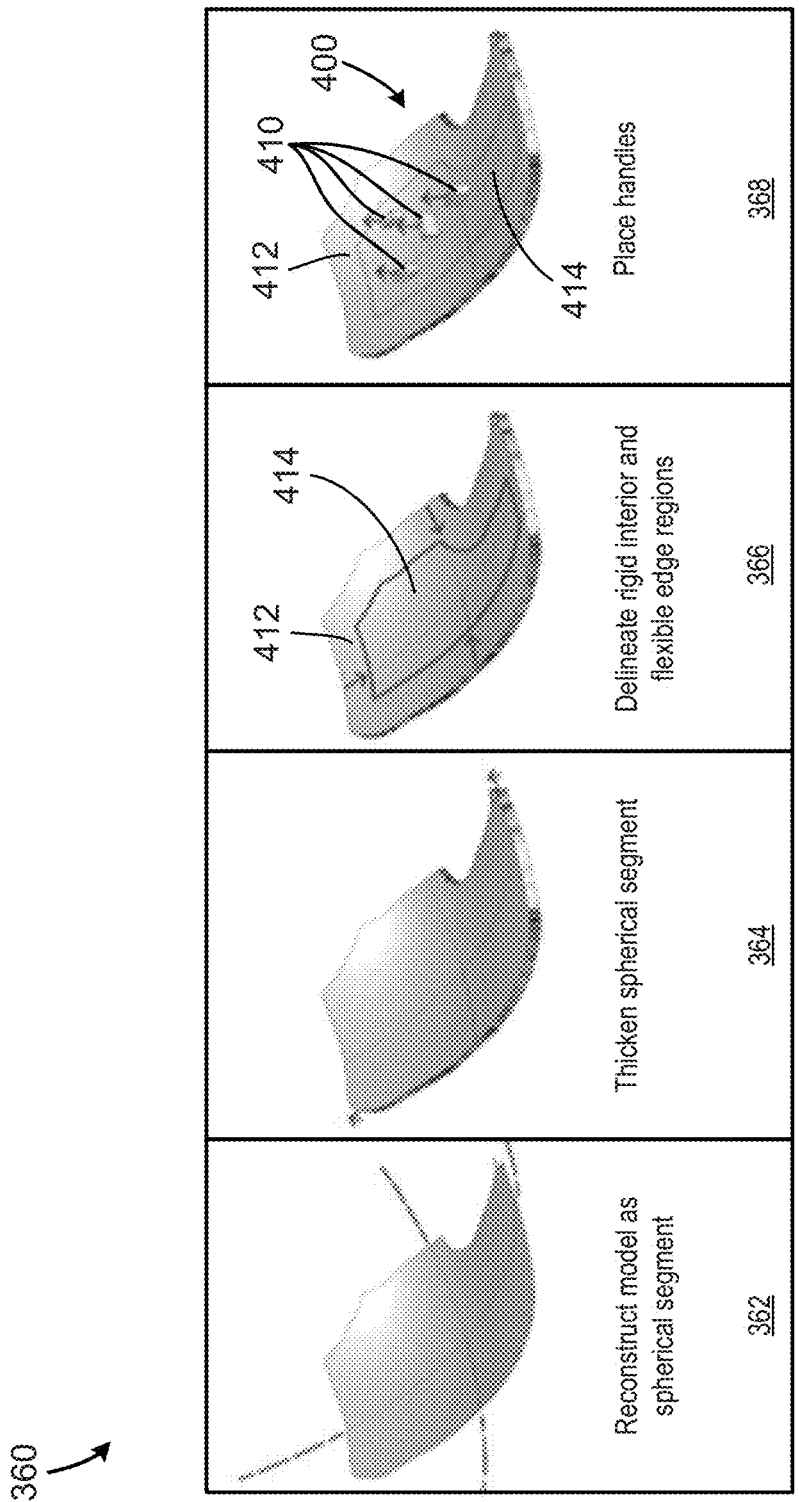
FIG. 7 is a process diagram of a method for processing a defect model to create a prosthetic device model.

FIG. 7 illustrates a method 360 of processing a 3D computer model to create a model of a prosthetic device 400. At step 362, the computer model is reconstructed as a spherical segment, for example using imaging data of the subject's body part. In the illustrated embodiment, the spherical segment is selected based on a best-fit sphere of the computer model. The spherical segment is then thickened according to the specific body part the prosthetic device 400 is to be used with. The desired thickness can also depend on the materials the prosthetic device 400 will be formed with and the desired flexibility of the prosthetic device 400. In some embodiments, other factors can be used to determine the desired thickness.

Once thickness has been added, the regions of a flexible edge 412 and the rigid interior 414 are delineated by offsetting model boundaries inward by a desired offset distance at step 366. In some embodiments, the desired offset distance can alternatively or additionally be a function of a size requirement for insertion into a subject, the materials the prosthetic device will be formed with, and/or the desired flexibility. As described above, a transition from rigid interior 414 to flexible edge 412 may be gradual or abrupt. At step 368, handles 410 are mapped at specific locations on the prosthetic device 400. The position of each handle 410 can be selected based on proximity to reference points on the subject's body that will be easily identifiable during surgery.

After completing the processing method 360, the physical prosthetic device can be manufactured. When the prosthetic device is manufactured, the rigid interior 414 and the flexible edge 412 can be formed from a first material and second material, respectively, as described above with respect to FIGS. 1-3. In the illustrated embodiments, the prosthetic devices can be produced using a multi-material 3D printer. For prosthetic devices with abrupt transitions from a first material to a second material, a two-part mesh is sent to the 3D printer for production. For prosthetic devices with gradual transitions from a first material to a second material, a graded material interface must be applied at the interface between the first and second materials In some embodiments, alternative manufacturing processes, such as molding and extrusion techniques, can be used to create a prosthetic device. Further, in some embodiments, multiple manufacturing techniques may be used to produce one or more portions of the prosthetic devices separately, requiring additional device assembly before use.

Figure 8:
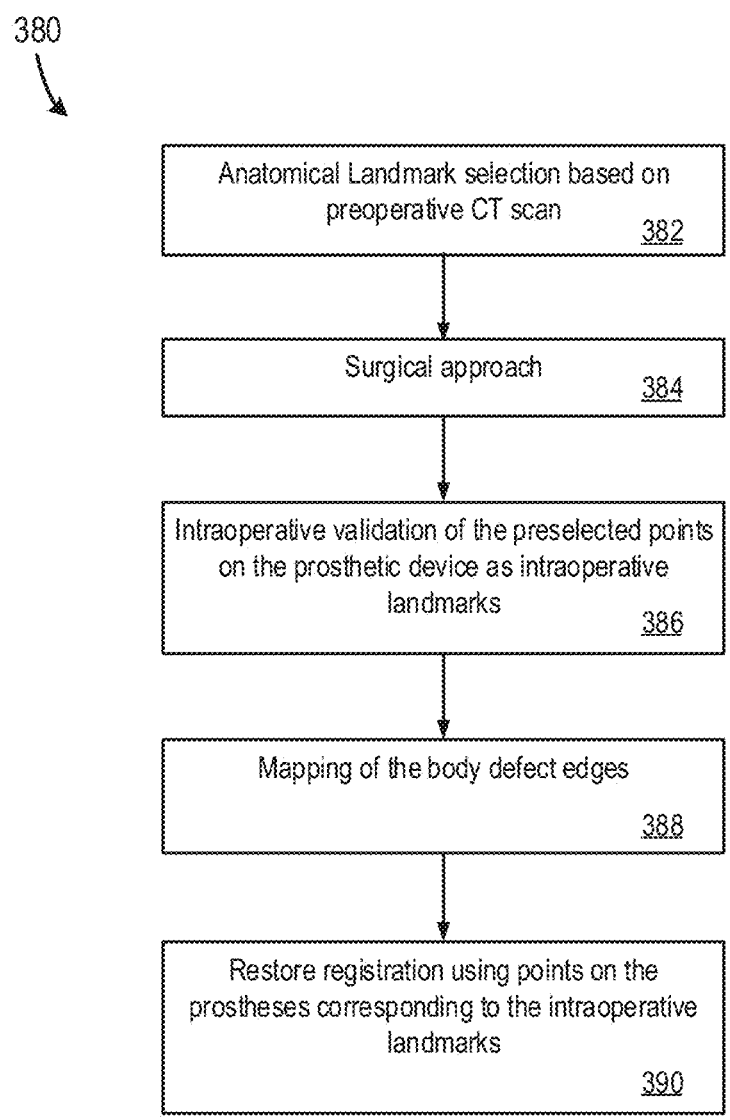
FIG. 8 is a process diagram of a method for adjusting a prosthetic device using neuronavigation transfer data.

Referring to FIG. 8, a method 380 for adjusting a prosthetic device is illustrated. At step 382, anatomical landmarks can be selected based on preoperative imaging (e.g., a preoperative CT scan), and these landmarks can be registered to the prosthetic device model. In the illustrated embodiment, the same set of landmarks can be used to guide handle placement in the model processing method 360 of FIG. 7, however, other embodiments may use other landmarks. Once the preoperative landmarks have been selected, the surgical approach is implemented at step 384, thereby creating the surgical defect. In embodiments where the defect is non-surgical, step 384 can include accessing the non-surgical defect. This surgical approach may signify the beginning of an implantation procedure.

At step 386, the preoperative anatomical landmarks are validated intraoperatively, thus creating intraoperative landmarks. The edges of the body defect are then mapped intraoperatively at step 388. This mapping of the defect is used to trace the extent of the defect on to the preoperative CT scan. In step 390, an image registration is restored using the intraoperative landmarks on the prosthetic device model. Utilizing this neuronavigation transfer (e.g., intraoperative tracing of the defect with the restored registration), a printed prosthetic device can then be tailored to the defect based on intraoperative data.

Figure 9:
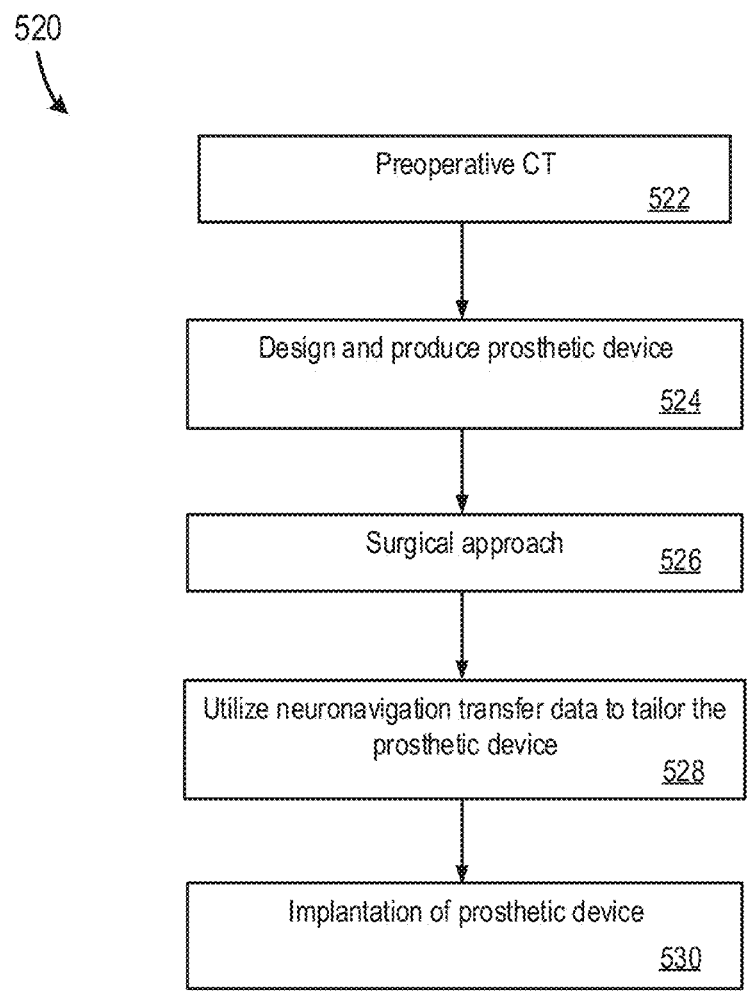
FIG. 9 is a process diagram of producing and using a prosthetic device.

Referring to FIG. 9, an exemplary embodiment of a method 520 for making and using a prosthetic devices is illustrated. According to the illustrated embodiment, preoperative image data (such as a preoperative CT scan) is acquired at step 522. Using the acquired image data, a prosthetic device is modeled and manufactured in step 524. In the illustrated embodiment, the design of the prosthetic device incorporates steps for producing a model discussed in connection with FIG. 4 and steps for processing the model discussed in connection with FIG. 7. In other embodiments, however, alternative steps for designing and creating a prosthetic device can be used in combination with, or in place of, any combination of step disclosed herein.

Figure 10:
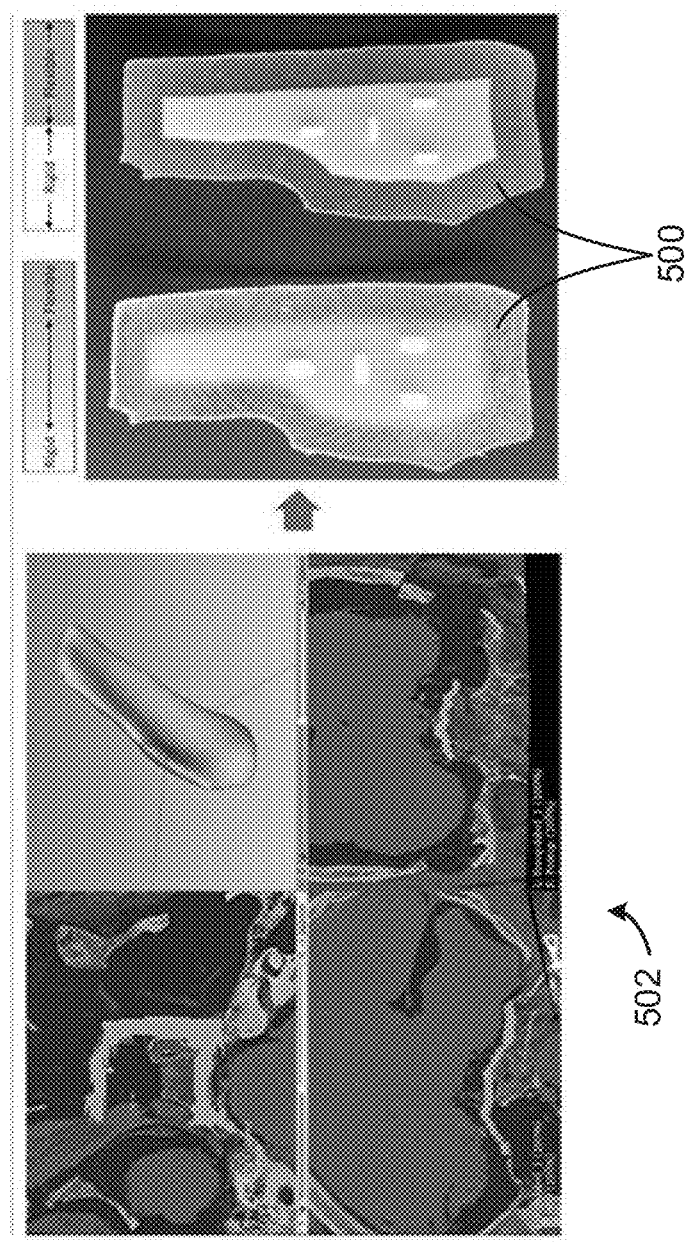
FIG. 10 is an example image illustrating a model and a prosthetic device produced according to the method of FIG. 9.

Following the creation of the prosthetic model, the surgical approach is implemented at step 526, thereby creating a surgical defect in the subject's body (or accessing a non-surgical defect). Step 528 then utilizes neuronavigation transfer data to tailor the prosthetic device in accordance with one or more steps discussed in connection with FIG. 8. After final modifications are made, the prosthetic device is implanted in the subject, e.g., via an endoscopic procedure, at step 530. FIG. 10 illustrates two prosthetic devices 500 as well as models 502 created according to the method 520 for making and using a prosthetic devices.

Figure 11:
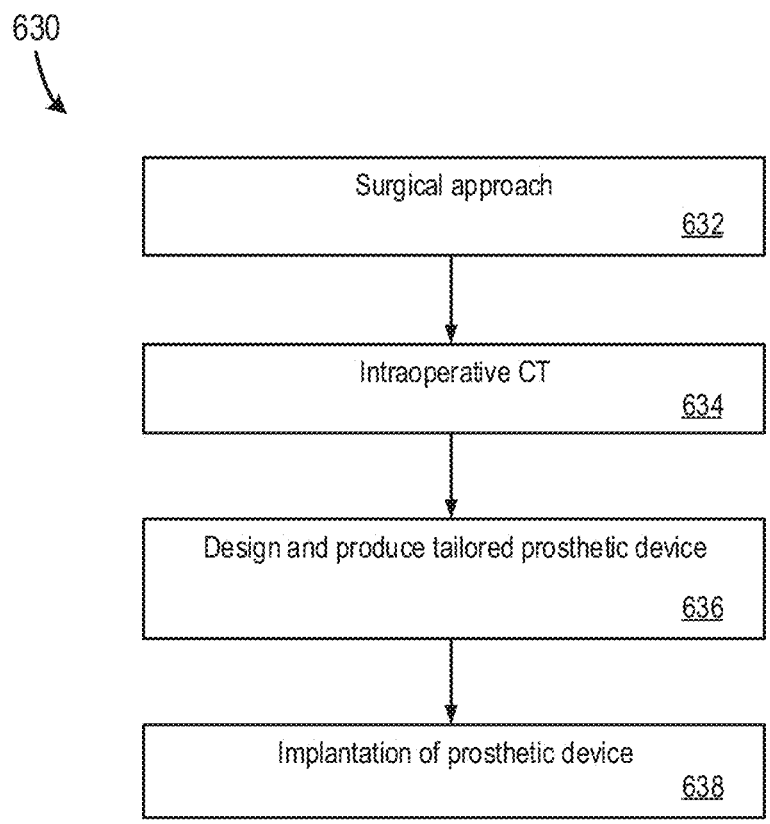
FIG. 11 is a process diagram of intraoperatively producing and using a prosthetic device.
Figure 12:
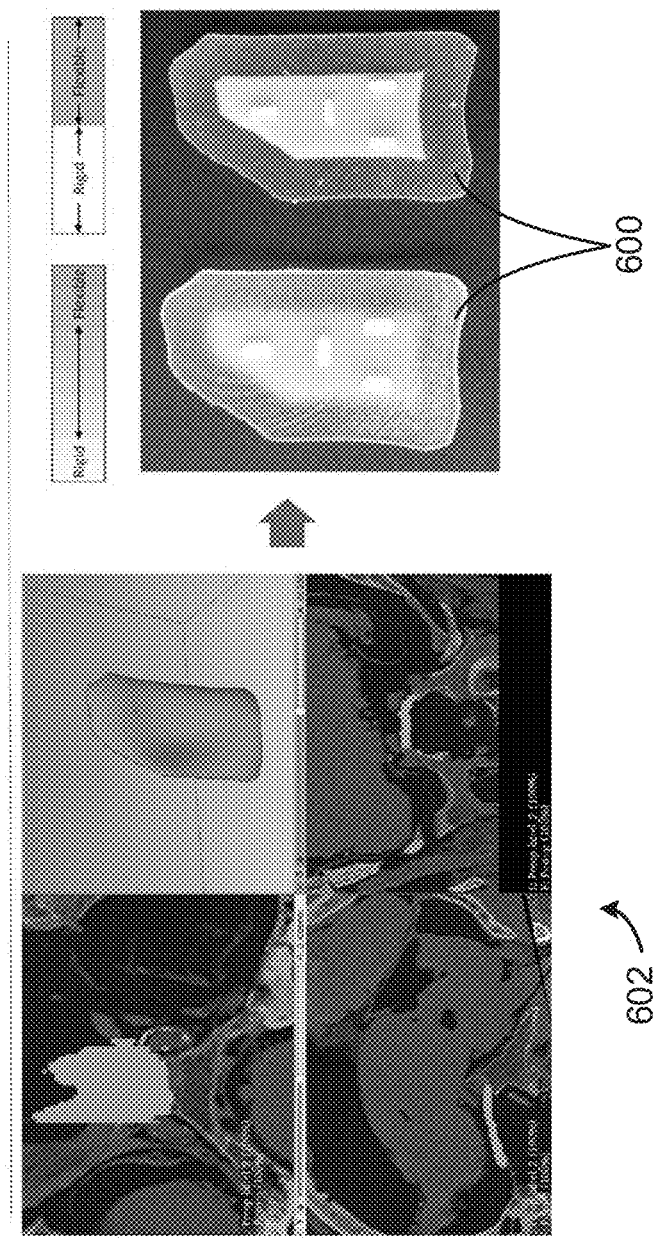
FIG. 12 is an example image illustrating a model and a prosthetic device produced according to the method of FIG. 9.

Referring to FIG. 11, another exemplary embodiment of a method 630 for intraoperatively making and using a prosthetic devices is illustrated. First, a surgical approach is implemented in step 632, thereby creating a surgical defect. Following the surgical approach, intraoperative image data is acquired (e.g., via an intraoperative CT scan) at step 634. The acquired data from step 634 is used at step 636 to model, produce, and tailor a prosthetic device based on the specific surgical defect. Finally, the prosthetic device is implanted in the subject, e.g., using an endoscopic procedure, at step 638. FIG. 12 illustrates two prosthetic devices 600 as well as models 602 created according to the method 630 for intraoperatively making and using a prosthetic devices. Accordingly, the method 630 of FIG. 11 differs from the method 520 of FIG. 10 in that all design and modeling of the prosthetic device is completed intraoperatively.

The following study description sets forth, in detail, ways in which the present disclosure may be used or implemented, and will enable one of skill in the art to more readily understand the principles thereof. The following example is presented by way of illustration and is not meant to be limiting in any way. The production and use of multiple prosthetic devices is more particularly described in the following example which is intended for illustration purposes only, since numerous modifications and variations will be apparent to those skilled in the art. As such, any details of the below example may be implemented with any of the devices and methods described above.

Scanning and Approaches

Three silicone-injected cadaveric specimens were used for a study in accordance with aspects of the invention. Preoperative thin-cut volumetric bone-window CT scans were performed, allowing segmentation of extended prosthetic models of the skull base. A different endoscopic extended endonasal approach was performed in each specimen: a transplanum transsphenoidal approach to the sellar/suprasellar region; a transcribriform transplanum approach with partial opening of the sella floor; and a transclival approach extending from the floor of the sella to the inferior third of the clivus. The specimens underwent post-procedure thin-cut CT scans, equivalent to intraoperative imaging, enabling the segmentation of the defect and the direct tailoring of the prosthetic device based on the intraoperative conditions. In total, for each cadaver, two sets of prosthetic devices were prepared: an extended skull base model (Ex-Model) based on preoperative CT scans, and a tailored model (T-model), modeled directly according the defect seen on the intraoperative scans.

Modeling and 3D Printing

DICOM image reconstruction and segmentation was performed on a 3D Slicer. In order to ensure device stability while allowing maneuverability through tight nasal cavities, the models were designed to have a rigid core and flexible edges. With regards to the center/edge material interface, both abrupt and gradual material transitions were explored. Post-processing was carried out on segmented meshes (.stl formats) of both Ex- and T-models to ensure consistent thickness, vary material properties, and add in positioning handles. Post-processing was carried out in Rhinoceros 3D. This involved reconstructing the model as a spherical segment by identifying the best-fit sphere to the segmented mesh. The segment was then thickened to 1 millimeter (mm) and the outline of the segment was offset inwards by 3 mm, delineating rigid interior and flexible edge regions. Locations of positioning handles were identified within the rigid interior region and were placed along the normal to the thickened spherical segment at the insertion point. A two-part mesh representing two materials with an abrupt transition was then exported to the printer. An additional step was required to introduce a functional material gradient between the rigid and flexible regions. Taking advantage of the ability of modern multi-material 3D printers to create digital materials with intermediate material properties between the two source resins, a graded material interface was incorporated between the rigid and flexible phases. Prototypes were printed on a Connex500 multi-material 3D printer. At each print layer, flexible and rigid material photopolymers of different colors were simultaneously ejected and eventually UV-cured into a single build. The materials used for the core and the edge were rigid white VeroWhitePlus® and flexible transparent TangoPlus®. These two materials represented the extremes along the rigidity scale with the Vero family being the stiffest and the Tango family the most flexible, representing an approximate 1000-fold modulus difference—the Vero being about 1 GPa (gigapascals) and the Tango about 1 MPa (megapascals).

Navigation Transfer, Tailoring, and Implantation

The T-model prostheses, based on intraoperative CT scans, were directly implanted into the bony defects, while the Ex-Models were tailored to the operative defect using neuronavigation transfer data. An intraoperative landmarks acquisition method (available on a clinically available neuronavigation system) was used to transfer the registration to the Ex-Model. When designing the models, handle positions were selected near specific reference points easily identifiable during surgery (e.g., floor of the sella, sphenoidal sinus septal base, etc.). After registering the cadavers to the preoperative CT scan and completing the nasal portion of the approach, these same reference point landmarks previously planned on preoperative scans as intraoperative landmarks were acquired. A minimum of four landmarks were selected for each cadaver, according to the models' handles. After the skull base defect was created, multiple points along its edges were acquired to trace the extent of the defects on the preoperative CT scan. The next step was performed using the "restore registration with intraoperative points" feature on the navigation system. Points on the Ex-models corresponding to the previously acquired landmarks on the cadaver's skull base were selected as intraoperative landmarks. The software was instructed to restore the registration using these acquired intraoperative landmarks, which allowed the registration from the cadaveric head to be transferred onto the Ex-model. The tracing of the operative defect was then used to help tailor the Ex-model. The tailoring of the models was possible with ordinary surgical scissors given the relatively flexible nature of the material edges.

Results

In all three cadaver heads, the T-Models, constructed based on the intraoperative CT featuring the created skull base defects, underestimated the size of the defect in one or two dimensions. The use of intraoperative landmark acquisition for navigation transfer was sufficiently accurate to allow navigation on the Ex-models as if the pointer was still on the skull base. The navigation transfer offered sufficient precision to help tailor the Ex-models. The model was oversized by 5 mm, given the insight provided by the results of the first experiment with the T-Models. The successful and stable Ex-Models implantation was possible in all three cadavers. The semi-transparent feature of the material used for the printing helped visualize the edges of the skull base defect facilitating the subdural insertion of the model under direct visual control of surrounding structures. No major differences were noticeable between model implantations in the anterior, middle, and posterior skull base defects. From a rigidity perspective, the models with a central rigid core and progressively flexible edges offered good maneuverability for implantation, as well as good stability. The flexibility of the models' edges facilitated the introduction of the models through the nostril and maneuvering inside the nasal cavity.

Discussion

In the above study, three-dimensional variability of surgical defects was addressed as one principal reconstruction challenge. Skull base defects can vary according to the tumor location and the bone removal required, the tumor's relationships to important neurovascular structures, and the specific nasal and bony anatomy of the subject. The use of 3D printing to endoscopically reconstruct skull base defects has not previously been assessed. The results of the study support that multi-material 3D printed skull base reconstruction prostheses, described herein, can be successfully modeled, printed, and implanted. It was verified that defect modeling can be successfully performed based on preoperative scans. The results also confirmed that, using currently available commercial systems and preselected landmarks on preoperative CTs, with the methods described herein, it is possible to transfer a sufficiently precise registration that can guide a surgeon in tailoring a preprinted skull base model prosthesis.

The use of neuronavigation transfer using preoperatively selected landmarks matched to references on the printed models was feasible using currently available clinical neuronavigation software. This novel (off-label) use of intraoperative landmark acquisition opens the possibility of tailoring the preprinted skull base model according to intraoperatively collected points corresponding to the defect edges. This would avoid the need for multiple nasal insertions and decrease the risk of miscutting the preprinted model. Furthermore, the surgeon can always return to the original patient image registration by going back to the previous registration solution, as long as the navigation reference array remains in its original position.

In accordance with embodiments of the present invention, 3D printing of a defect based on an intraoperatively acquired CT scan can be achieved with sufficient modeling and printing speeds. It would be possible to acquire an early intraoperative CT scan (such traditional or cone beam computed tomography) once the bony opening is completed, giving sufficient time for modeling, printing, and sterilizing the 3D model while the surgeon is performing the tumor resection.

It was also determined that, during endoscopic endonasal surgery, when the sellar floor is opened, simply recreating its concave shape may allow accumulation of CSF facing the construct and would represent an increased risk of CSF fistula formation. By adopting a less concave curvature for the defect in a prosthetic device, particularly between the planum, tuberculum, and the superior edge of the clivus, a small convex curvature will preclude CSF from stagnating without exerting pressure on the intradural structures. Furthermore, modeling the skull base defect directly from intraoperative CT image can be even more challenging as the tailored models in the study underestimated the size of the defect. However, in accordance with aspects of the invention, a systematic addition of, e.g., 5-10 mm in both the coronal and particularly sagittal dimension would appear to correct this issue. Additionally, after modeling the three-dimensional surface of the defect, handles were added on the inferior nasal surface of the implant. The handles helped maneuver the defect inside the nasal cavity and served also as landmarks for directing the registration transfer. Accordingly, a second model that differs from the original (first) model can be created to account for these adjustments.

Additionally, the use of a flexible material for the models' edges may lessen the risk of anatomical damage during placement. Partial folding of the model could decrease risk of injuring the nasal mucosa. The flexible edges can be particularly helpful during implantation, while the central rigid core offers the necessary rigidity to hold the prosthetic device in place. Also, the flexible and smooth nature of these edges could decrease risk of injury to surrounding structures during insertion. The semitransparent feature of the flexible portions of the models can also be helpful during insertion. The rigidity gradient design can offer a stable construct distributing tension across the model with good flexibility for placement and rigidity for implant stability. Further, functionally graded interfaces offer advantages in that they can reduce or eliminate stress concentrations at the junctions between rigid and flexible phases in 3D printed constructs. Although the location and design of the graded interfaces in the models in the study were chosen such that they simply followed the external contours of the modeled geometry, in some embodiments, use of a finite element simulation may be used in order to create a more robust form factor.

In light of the above, embodiments of the invention provide for 3D printing of individual-specific skull base models for, for example, extended endoscopic endonasal surgery. A stable reconstruction can be created by spatial modeling and refinements, including smoothing out certain anatomical features and generally increasing model size, based on preoperative and/or intraoperative image data and by using multiple materials with a flexibility gradient. Furthermore, neuronavigation can help tailor preprinted prosthetic devices.

The invention claimed is:

1. A prosthetic device for a subject, the prosthetic device comprising:
   a first material;
   a second material surrounding at least a portion of a perimeter of the first material, the second material being more flexible than the first material; and
   one or more handles coupled to and protruding outwardly from one of the first material or the second material,
   the first material and the second material having a resting shape configured to fit a body part of the subject,
   the second material being deformable to fit the prosthetic device through an opening of the subject smaller than the resting shape to reach the body part, and
   wherein the second material is progressively more flexible from an inner edge adjacent the first material to an outer edge.

2. The prosthetic device of claim 1, wherein an interface between the first material and the second material is a gradual change from the first material to the second material.

3. The prosthetic device of claim 1, wherein the resting shape is modeled using CT imaging of the subject.

4. The prosthetic device of claim 1, wherein the resting shape is formed using three-dimensional printing.

5. The prosthetic device of claim 1, wherein the resting shape generally matches a portion of the subject's skull.

6. The prosthetic device of claim 5, wherein the resting shape includes one or more characteristics that differ from an anatomical feature of the subject's skull.

7. The prosthetic device of claim 6, wherein the anatomical feature is a sella.

8. A prosthetic device for a subject, the prosthetic device comprising:
   a first material;
   a second material surrounding at least a portion of a perimeter of the first material, the second material being more flexible than the first material; and
   one or more handles coupled to and protruding outwardly from one of the first material or the second material,
   the first material and the second material having a resting shape configured to fit a body part of the subject,
   the second material being deformable to fit the prosthetic device through an opening of the subject smaller than the resting shape to reach the body part, and
   wherein an interface between the first material and the second material is a gradual change from the first material to the second material.

9. The prosthetic device of claim 8, wherein the resting shape is modeled using CT imaging of the subject.

10. The prosthetic device of claim 8, wherein the resting shape is formed using three-dimensional printing.

11. The prosthetic device of claim 8, wherein the resting shape generally matches a portion of the subject's skull.

12. The prosthetic device of claim 11, wherein the resting shape includes one or more characteristics that differ from an anatomical feature of the subject's skull.

13. The prosthetic device of claim 12, wherein the anatomical feature is a sella.

* * * * *